(12) United States Patent
Bishop et al.

(10) Patent No.: US 10,380,531 B2
(45) Date of Patent: *Aug. 13, 2019

(54) TASK-BASED BIOMETRIC DIFFERENTIATOR OF STRESS LEVELS TO MAXIMIZE PRODUCTIVITY

(71) Applicant: International Business Machines Corporation, Armonk, NY (US)

(72) Inventors: Adam T. Bishop, Roanoke, VA (US); Matthew R. Catalfamo, Clay, NY (US); Al Chakra, Apex, NC (US); Indrajit Viswanath, Atlanta, GA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 472 days.

This patent is subject to a terminal disclaimer.

(21) Appl. No.: 14/879,240

(22) Filed: Oct. 9, 2015

(65) Prior Publication Data
US 2017/0046642 A1    Feb. 16, 2017

Related U.S. Application Data

(63) Continuation of application No. 14/821,978, filed on Aug. 10, 2015.

(51) Int. Cl.
*G06Q 10/06*    (2012.01)
*A61B 3/11*    (2006.01)
(Continued)

(52) U.S. Cl.
CPC .......... *G06Q 10/0639* (2013.01); *A61B 3/112* (2013.01); *A61B 5/0205* (2013.01);
(Continued)

(58) Field of Classification Search
CPC .................................................. G06Q 10/0639
(Continued)

(56) References Cited

U.S. PATENT DOCUMENTS

| 2014/0278629 | A1* | 9/2014 | Stephenson | G06Q 10/1091 705/7.13 |
| 2015/0305675 | A1* | 10/2015 | Miller | A61B 5/0205 600/301 |
| 2016/0286047 | A1* | 9/2016 | Matula | G06Q 10/06311 |

OTHER PUBLICATIONS

Kristina Grifantini, Sensor Detects Emotions through the Skin, MIT Technology Review, Oct. 26, 2010. (Year: 2010).*

(Continued)

*Primary Examiner* — Nadja N Chong Cruz
(74) *Attorney, Agent, or Firm* — Cantor Colburn LLP; Teddi Maranzano

(57) ABSTRACT

An aspect includes receiving a request to assign a task to a user based on biometric data. Correlated data that correlates characteristics of tasks previously performed by the user with observed productivity and stress levels of the user while performing the tasks is accessed. An optimization model is applied to select a task that maximizes a predicted productivity of the user in performing the task while at the same time minimizes a predicted negative stress level of the user while performing the task. Input to the optimization model includes the correlated data and characteristics of a plurality of potential tasks. The selected task is assigned to the user. The correlated data for the user is updated based on the observed productivity of the user in performing the selected task, the observed stress level of the user while performing the selected tax, and at least one characteristic of the selected task.

9 Claims, 4 Drawing Sheets

(51) Int. Cl.
  *A61B 5/0205* (2006.01)
  *A61B 5/053* (2006.01)
  *A61B 5/00* (2006.01)
  *A61B 5/16* (2006.01)
  *A61B 5/024* (2006.01)

(52) U.S. Cl.
  CPC .......... *A61B 5/0531* (2013.01); *A61B 5/0537* (2013.01); *A61B 5/165* (2013.01); *A61B 5/443* (2013.01); *A61B 5/4884* (2013.01); *A61B 5/7246* (2013.01); *G06Q 10/06311* (2013.01); *G06Q 10/06398* (2013.01); *G06Q 10/063114* (2013.01); *A61B 5/024* (2013.01)

(58) Field of Classification Search
  USPC ........................................................ 705/7.38
  See application file for complete search history.

(56) References Cited

OTHER PUBLICATIONS

Adam T. Bishop et al., Pending U.S. Appl. No. 14/821,978 entitled "Task-Based Biometric Differentiator of Stress Levels to Maximize Productivity," filed Aug. 10, 2015.
List of IBM Patents or Patent Applictions Treated as Related; (Appendix P), Filed Oct. 9, 2015, 2 pages.

* cited by examiner

TASK-BASED BIOMETRIC DIFFERENTIATOR OF STRESS LEVELS TO MAXIMIZE PRODUCTIVITY

DOMESTIC PRIORITY

This application is a continuation of U.S. patent application Ser. No. 14/821,978, filed Aug. 10, 2015, the content of which is incorporated by reference herein in its entirety.

BACKGROUND

The present invention relates to biometric feedback, and more specifically, to assigning tasks using a task-based biometric differentiator of stress levels to maximize productivity.

SUMMARY

According to embodiments of the present invention, a method, system, and computer program product are provided for assigning tasks based on biometric data. A request to assign a new task to a user is received and correlated data that correlates characteristics of tasks previously performed by the user with observed productivity and stress levels of the user while performing the tasks is accessed. Each observed stress level is either a negative stress level or a positive stress level. An optimization model is applied to select, from a plurality of potential tasks, a task that maximizes a predicted productivity of the user in performing the task while at the same time minimizes a predicted negative stress level of the user while performing the task. Input to the optimization model includes the correlated data and characteristics of the plurality of potential tasks. The selected task is assigned to the user. An observed productivity of the user in performing the selected task and an observed stress level of the user while performing the selected task are received. The observed stress level is obtained from a biometric sensor. The correlated data for the user is updated based on the observed productivity of the user in performing the selected task, the observed stress level of the user while performing the selected tax, and at least one characteristic of the selected task.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Embodiments described herein are directed to increasing worker productivity by using biometric data when assigning work items, or tasks. In accordance with embodiments, tasks are assigned based on the premise that a "happy" employee is a "more productive" employee. When an employee is working on an assigned task, biometric measurements of the employee are recorded in an attempt to assess an amount of stress that performing the task causes the employee. Characteristics of the task are correlated with the biometric measurement(s), and stored for use in future task assignments to the employee. Embodiments attempt to reduce the employee's stress level by assigning tasks that have characteristics in common with tasks previously performed by the employee that have caused the employee the least amount of negative stress.

An example scenario where an embodiment may be utilized follows. An employee, "Rob", is a member of a software team that is managed by another employee, "John." Rob has been getting tasks assigned to him that he doesn't like, while there are other tasks that need to be done that he would prefer. Since Rob doesn't like the tasks that he is assigned and they induce stress, his productivity level is being negatively affected. For example, he is taking longer than expected to compete tasks, which directly affects the efficiency of the software team. Rob does not want to report to John that he doesn't like the tasks that are being assigned because he doesn't want his boss to think that he can't perform the job. Rob believes that he would be able to perform tasks at a higher rate of productivity if he enjoyed the tasks that John assigned him. Being the manager of the software team, John believes that he is assigning tasks fairly because he doesn't receive any complaints. Embodiments described herein can give John a way to receive voluntary feedback from his team members based on their biometric reactions to the assigned tasks, and using this information John can assign tasks to his team more strategically and increase the overall productivity of the team.

Embodiments include an "opt-in" system which allows each user to decide whether or not to allow biometric measurements to be recorded and used by the system for use in task assignment to the user. When a user opt-out of having biometric measurements being recorded, the system can use a default value for the biometric measurement.

Figure 1:
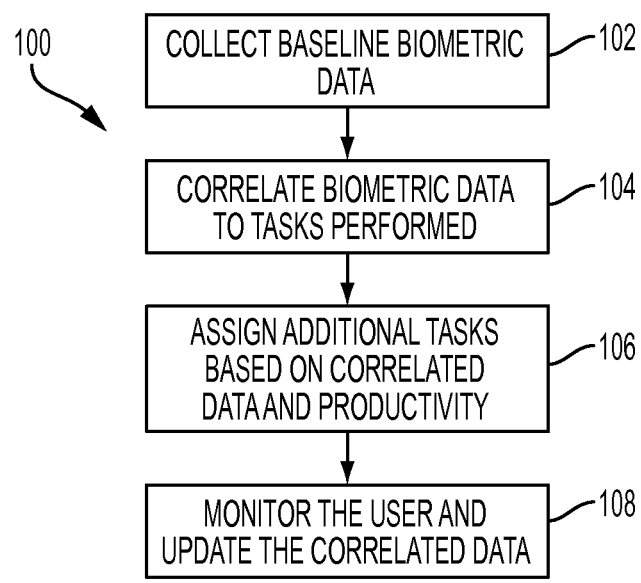
FIG. 1 depicts a process flow for assigning tasks based on biometric data in accordance with an embodiment.

Referring now to FIG. 1, a process flow 100 for assigning tasks based on biometric data is generally shown in accordance with an embodiment. In an embodiment, the processing shown in FIG. 1 is performed by task management application executing on one or more processors. At block 102, baseline biometric data is collected for a user, the collecting including recording the user's level of stress at various points in the day while performing known tasks. At the same time, information about the tasks that the user is performing while the baseline biometric data is being collected is recorded. The information can include, but is not limited to characteristics of the tasks and productivity of the user in performing those tasks. The data collection at block 102 can be performed for a specified time period such as four to six weeks to establish a baseline. See FIG. 2 and the accompanying description below for a more detailed description of an embodiment of the process performed at block 102 for establishing a baseline.

At block 104, the biometric data is correlated to the tasks that were performed. In an embodiment, the correlation is performed using a statistical data analysis package, or program, that can be used to correlate the productivity in a category of work to the levels of stress detected while dealing with those categories. The category of work can be expressed in terms of one or more characteristics. In the computer programming field these characteristics can include a type of programming language (e.g., JAVA, C, etc.) and a type of task (e.g., coding, debugging, design, integration testing, etc.). Any known statistical software package that correlates multiple data inputs (e.g., stress levels and tasks) in order to determine trends can be utilized by embodiments. Examples of statistical software packages include, but are not limited to the open source statistical package R and Minitab from Minitab Incorporated.

The statistical software package can be utilized to determine the level and type of stress (e.g., positive stress, negative stress) on the user associated with particular types of tasks. As used herein, the term "stress" refers to changes in a person's emotions due to external stimuli. These changes can be positive or negative. The term "positive stress" refers to stress that indicates that a person feels better about a task, which can lead to increased productivity. In contrast, the term "negative stress" refers to changes in a person that lead to decreased productivity. Positive stress and negative stress can be measured against a baseline stress level that is measured when a person is in non-stress/focus situations (e.g., a resting heart rate or relaxed phased pupil dilation).

In an embodiment, the statistical package graphs the biometric feedback data (e.g., the biometric measurements) and the productivity data (e.g., time spent and percentage of task completed, and/or expected completion date and actual completion date) for tasks performed by the user. For example, if a task takes the user longer to complete than expected (and/or the user completes the task late) and the task is associated with a high level of stress, then in an embodiment the statistical package can determine that the stress is negative stress indicating that the user did not enjoy performing the task. Conversely, if a task is performed on time and/or in less time than expected and the task is associated with a high level of stress, then in an embodiment the statistical package can determine that the stress is positive stress indicating that the user enjoyed performing the task.

In embodiment, the output from the statistical package (e.g., a correlation between a task and a negative or positive stress level) is used to generate correlated data for the user. The correlated data matches characteristics or categories of the tasks to negative and positive stress levels. For example, based on characteristics associated with the tasks, it can be determined that a particular user likes tasks that involve interacting with other employees and does not like tasks that have little social interaction. In another example, it can be determined that the user likes tasks having to do with debugging computer code but does not like tasks having to do with writing new computer code. Additional levels, besides like and dislike, can be implemented by embodiments. For example, there could be three or more levels representing a scale from like to neutral to dislike.

In addition, the user can also enter input to indicate that there are other factors impacting the user's stress level and/or productivity on a particular day (or other time span). These other factors may have nothing to do with the assigned tasks and instead be related to external stimuli. External stimuli can include, but are not limited to the user's health, fatigue, and/or family issues. These other external factors can be taken into account by the statistical analysis and/or when generating the correlated data. In an embodiment, the external factors registered by the user allows for accounting of statistical anomalies, such as a larger value of standard deviation from the mean level of stress.

Referring back to FIG. 1, at block 106, additional, or new, tasks are assigned to the user based on the correlated data. At block 108, the biometric feedback of the user is monitored while performing the additional tasks and the correlated data is updated based on the monitoring. The generation of the correlated data can take into account a learning curve when a user has been assigned to a new project or to a new type of task (or a task that the user has not performed in a while). In one embodiment this is performed by waiting for a specified number of times that the user performs a task having specified characteristics before generating the correlated data for that category of task. In addition, embodiments can be utilized to determine how long it takes a particular user to learn new skills. See FIG. 3 and the accompanying description below for a more detailed description of an embodiment of a process for performing the task assigning of block 106 and the monitoring of block 108.

Figure 2:
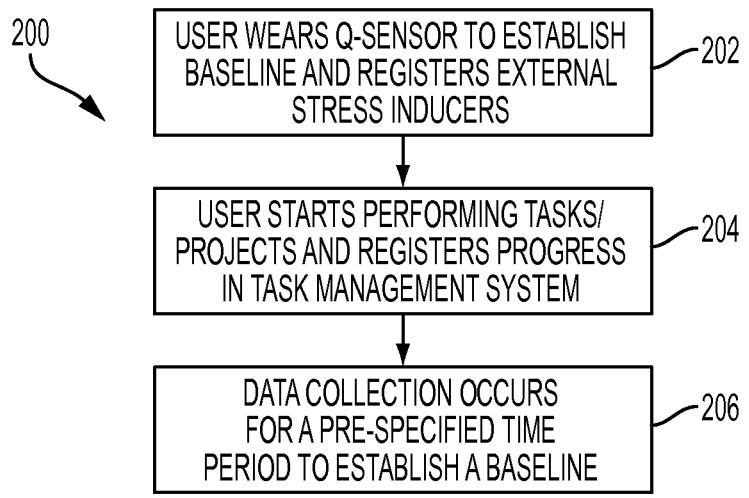
FIG. 2 depicts a process flow for establishing a biometric baseline in accordance with an embodiment.

Referring now to FIG. 2, a process flow 200 for a data collection phase that includes establishing a biometric baseline is generally shown in accordance with an embodiment. In an embodiment, the processing shown in FIG. 2 is performed by a task management computer application executing on one or more processors. At block 202, a user wears a biometric sensor, such as a Q-sensor, to record biometric measurements. In addition, the user can register external stress inducers such as health, fatigue, and/or family issues. As known in the art, a Q-sensor can be worn as a bracelet and used to measure electro-dermal activity through the use of skin resistance.

When a Q-sensor is used to collect biometric measurements, the term "tonic skin conductance" or "skin conductance level (SCL)" refers to the level of skin conductance when the person is not subject to any known discrete environmental event or external stimuli. Tonic skin conductance levels typically vary slowly over time (e.g., over tens of seconds to minutes) based on a person's psychological state, hydration, skin dryness, and autonomic regulation. "Phasic skin conductance" or "skin conductance response (SCR)" can be associated with short-term events and occur in the presence of discrete environmental stimuli (e.g., sight, sound, smell, cognitive processes that precede an event such as anticipation, decision making, etc.). Phasic changes usually show up as abrupt increases in the skin conductance or peaks in the skin conductance. For example, if a software developer enjoys coding in Java and the project he is working on primarily uses that language then he is more likely to be happy with his work. These stress levels would then be measured by SCL. However if the same person is coding in C++, which he is new to, and has a presentation due soon this biometric feedback would be characterized by SCR.

Any type of biometric sensor that can record biometric measurements of a user can be implemented by embodiments. Other sensors that can be worn, or attached, to the user include, but are not limited to heart rate monitors and Fitbits. Additional biometric sensors that are not attached to the user can also be utilized by embodiments. These sensors can be contained in a computer device utilized by the user and include, but are not limited to pupil dilation detectors. In embodiments a single biometric sensor is utilized. In other embodiments, biometric measurements from two or more biometric sensors are combined to determine a user's stress level or other biometric measurement.

In an embodiment, all or portions of block 204 are performed simultaneously (or overlapping in time) with block 202. At block 204, the task management application is used by a manager or by the user to assign tasks (or projects made up of several tasks) to the user with clearly defined checkpoints and time frames. By completing these tasks or by reaching these checkpoints within the pre-decided time frames, the user's level of productivity can be measured through a percentage of work complete measurement. The user or manager can enter the task/checkpoint completion data into the task management application. In an embodiment the task management application interfaces to Rational Team Concert from IBM, however interfaces to other project management software applications can also be implemented by embodiments. At block 206, the process of blocks 202 and 204 is performed in a loop for a specified time period or until a specified number of tasks or checkpoints are completed. In an embodiment, the specified number of tasks may include a specified number of tasks having particular characteristics.

Figure 3:
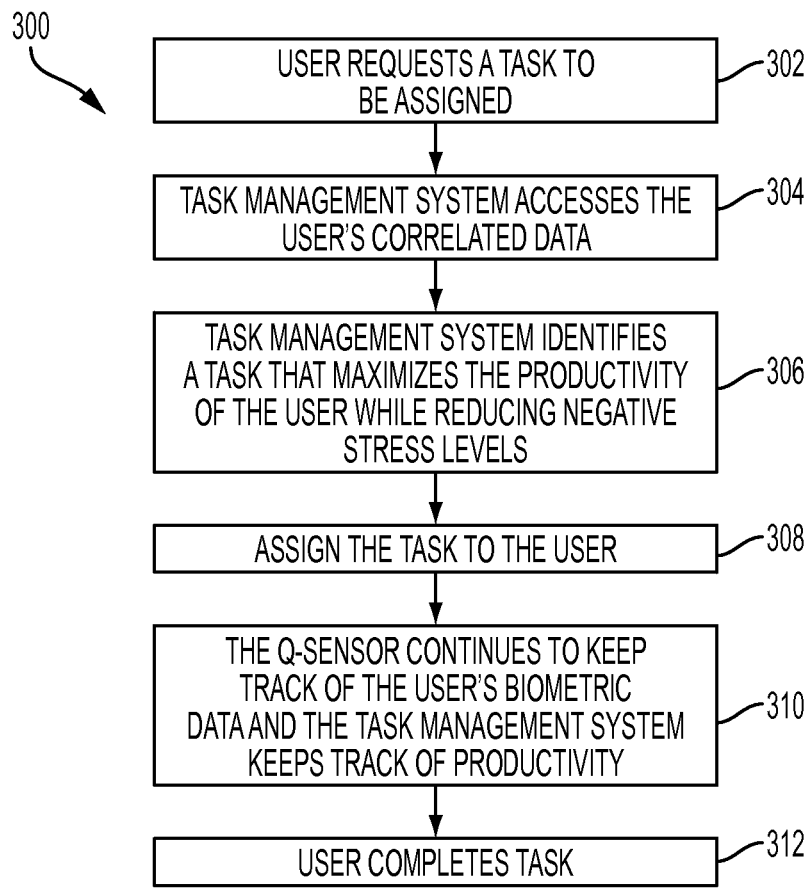
FIG. 3 depicts a process flow for assigning a new task and tracking biometric data of the user in accordance with an embodiment.

Referring now to FIG. 3, a process flow 300 for assigning a new task and tracking biometric data of the user is generally shown in accordance with an embodiment. In an embodiment, the processing shown in FIG. 3 is performed by a task management application executing on one or more processors. At block 302, a request to assign a new task to a user is received. The request can be received, e.g., from the user or from a project manager. At block 304, correlated data associated with the user is accessed. In an embodiment, the correlated data correlates characteristics of tasks previously performed by the user with observed productivity and stress levels of the user while performing the tasks. Each observed stress level is either a negative stress level or a positive stress level.

At block 306, a task that maximizes the productivity of the user while reducing negative stress levels is identified. This can be performed by applying an optimization model to select, from a plurality of potential tasks, a task that maximizes a predicted productivity of the user in performing the task while at the same time minimizes a predicted negative stress level of the user while performing the task. Input to the optimization model can include the correlated data and characteristics of the plurality of potential tasks. The plurality of potential tasks can be a list of tasks in a project plan that have not yet been assigned. In am embodiment, this optimization model has two major parts. The first is an objective function, which is generally a mathematical equation whose purpose is to identify the task that would maximize the user's productivity. This maximization function is constrained by the second part of the model, which includes a list of mathematical constraints. These constraints use inequalities to restrict the level of negative stress that the user is allowed to experience. These restrictions can be self imposed by the user based on factors like health and happiness. These two parts can then be fed into a program like Express Project or R to identify the best task for the user from the list of available tasks.

In an embodiment, the optimization is performed across a project with the correlated data of several users being taken into account. In this case the optimization model can sort through two lists. One list containing the users available to perform tasks and the other list contains a list of tasks. The optimization model could be applied to each combination of user and task based on a "bubble" sort technique.

In an embodiment, the selected task can be replaced (e.g., by a project manager) with a different task. A project manager can view all of the correlation data for the user, or the user and all of the team members combined. The system can suggest tasks for the user and/or other team members, and the project manager can agree to or override the suggestion(s). The project manager can select a different task than that suggested by the system for the user and cause the system to assign that different task (instead of the suggested task). In other embodiments, the task selection and assignment is completely automated and the system selects and assigns tasks to a user or group of users with the goal of maximizing productivity and/or lowering negative stress levels. I further embodiments, a hybrid system that includes a combination of manual task selection and automated task selection is implemented.

At block 308, the task is assigned to the user. In an embodiment, the assignment is performed by a task management application based on the optimization model output. Block 310 is performed to monitor the user while he or she is performed the task. In an embodiment, the monitoring produces data related to an observed productivity of the user in performing the selected task and an observed stress level of the user while performing the selected task (obtained, e.g., from a biometric sensor).

At block 312, the user completes the task. The correlated data for the user can then be updated based on the observed productivity of the user in performing the selected task, the observed stress level of the user while performing the selected task, and at least one characteristic of the selected task. In an embodiment, the observed productivity is based on one or more of: a comparison of an expected completion date and an actual completion date; and a comparison of an expected number of time units to complete the selected task and an actual number of time units to complete the selected task. The updating of the correlated data can include: based on the observed productivity, characterizing the observed stress level as a negative stress level or a positive stress level; associating the observed stress level and observed productivity with at least one characteristic of the selected task; and storing results of the associating as correlated data for the user. The updating can also take into a previous stress level and productivity associated with the selected task for example by storing an average or weighted average (or some other calculation) of the observed data and the previous correlated data. In addition, external factors can also be taken into account when updating the correlated data.

Figure 4:
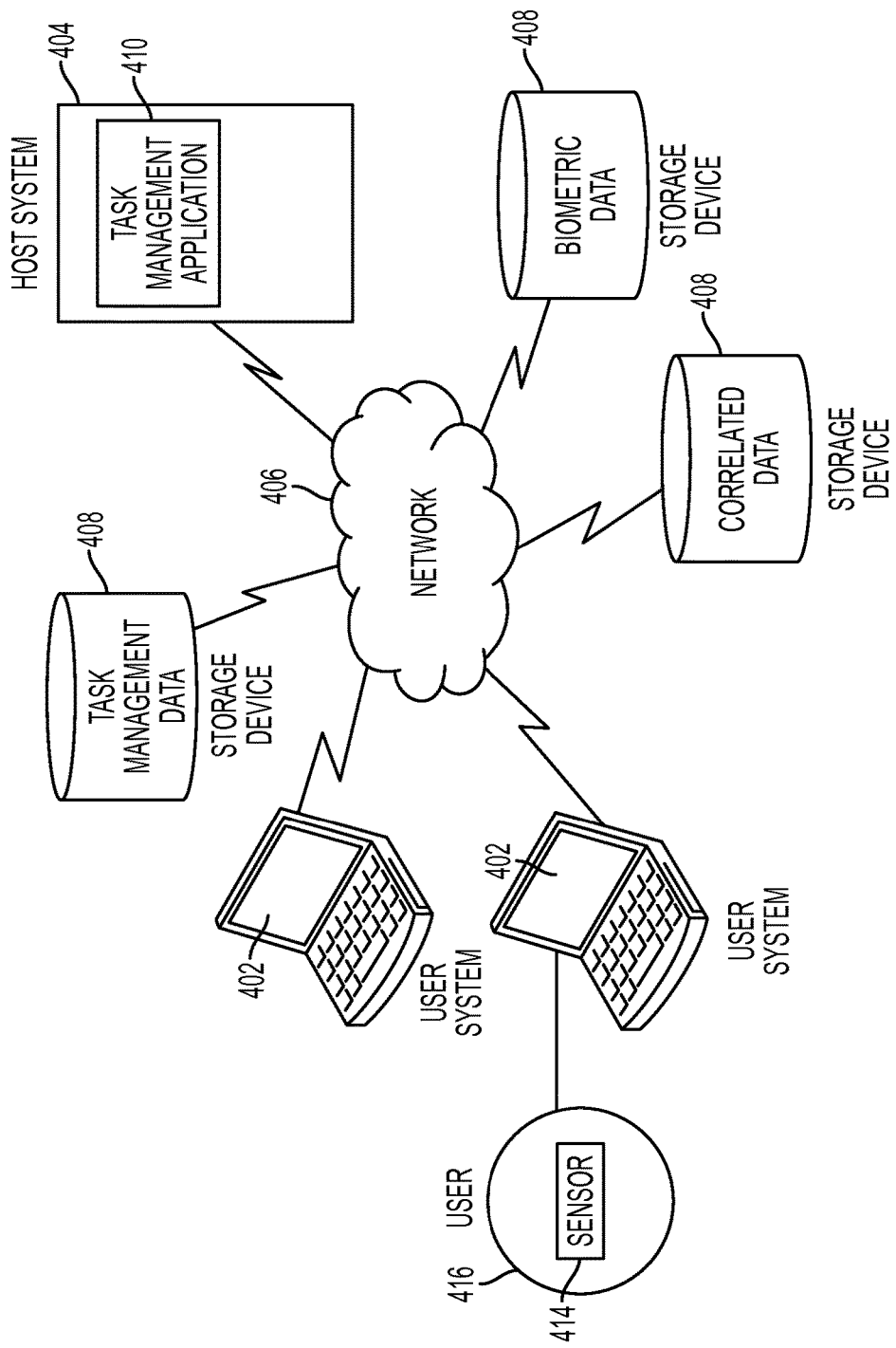
FIG. 4 depicts a block diagram of a system for assigning tasks based on biometric data in accordance with an embodiment.

Referring to FIG. 4, a block diagram of a system 400 for assigning tasks based on biometric data is generally shown in accordance with an embodiment. The system 400 includes a task management application 410 that is executed by one or more computer programs located on a host system 404 and/or a user system(s) 402.

The system 400 depicted in FIG. 4 includes one or more user systems 402 through which users at one or more geographic locations may contact the host system 404 to initiate programs. The user systems 402 are coupled to the host system 404 via a network 406. Each user system 402 may be implemented using a general-purpose computer executing a computer program for carrying out the processes described herein. The user systems 402 may be user devices such as personal computers (e.g., a lap top, a tablet computer, a cellular telephone) or host attached terminals. If the user systems 402 are personal computers, the processing described herein may be shared by a user system 402 and the host system 404. The user systems 402 may also include game consoles, network management devices, and field programmable gate arrays. In addition, multiple user systems 402 and/or host systems 404 may be concurrently operating to perform the processing described herein.

The network 406 may be any type of known network including, but not limited to, a wide area network (WAN), a local area network (LAN), a global network (e.g. Internet), a virtual private network (VPN), a cloud network, and an intranet. The network 406 may be implemented using a wireless network or any kind of physical network implementation known in the art. A user system 402 may be coupled to the host system through multiple networks (e.g., cellular and Internet) so that not all user systems 402 are coupled to the host system 404 through the same network. One or more of the user systems 402 and the host system 404 may be connected to the network 406 in a wireless fashion. In one embodiment, the network is the Internet and one or more user systems 402 execute a user interface application (e.g. a web browser) to contact the host system 404 through the network 406. In another exemplary embodiment, the user system 402 is connected directly (i.e., not through the network 406) to the host system 404. In a further embodiment, the host system 404 is connected directly to or contains one or more of the storage device 408.

The storage devices 408 include data relating to the tasks management application 410 and may be implemented using a variety of devices for storing electronic information. In an embodiment, data stored in the storage devices 408 includes, but is not limited to, task management data (e.g., tasks to be assigned, assigned tasks and responsible user, target due dates and percent complete data, etc.), biometric data (data generated by a sensor), and correlated data, and other data utilized by embodiments described herein. It is understood that the storage devices 408 may be implemented using memory contained in the host system 404 or that they may be separate physical devices. The storage devices 408 may be logically addressable as a consolidated data source across a distributed environment that includes the network 406. Information stored in the storage devices 408 may be retrieved and manipulated via the host system 404 and/or via a user system 402. Though shown as three separate storage devices 408 each holding different types of data, any number of other arrangements are also possible. Other non-limiting examples follow. For example, a single storage device 408 can contain all of the data pertaining to users and tasks on a particular project. In another example, a single storage device 408 can hold all of the data pertaining to one user. In another example, biometric data and correlated data for a user is stored on a storage device 408 located in the user system 402 and the task management data is stored on a storage device 408 located on the host system 404.

The host system 404 depicted in FIG. 4 may be implemented using one or more servers operating in response to a computer program stored in a storage medium accessible by the server. The host system 404 may operate as a network server (e.g., a web server) to communicate with the user system 402. The host system 404 handles sending and receiving information to and from the user system 402 and can perform associated tasks. The host system 404 may also include a firewall to prevent unauthorized access to the host system 404 and enforce any limitations on authorized access. For instance, an administrator may have access to the entire system and have authority to modify portions of the system. A firewall may be implemented using conventional hardware and/or software as is known in the art.

The host system 404 may also operate as an application server. The host system 404 executes one or more computer programs, including a task management application 410, to provide aspects of embodiments as described herein. Processing may be shared by the user system 402 and the host system 404 by providing an application to the user system 402. Alternatively, the user system 402 can include a stand-alone software application for performing a portion or all of the processing described herein. As previously described, it is understood that separate servers may be utilized to implement the network server functions and the application server functions. Alternatively, the network server, the firewall, and the application server may be implemented by a single server executing computer programs to perform the requisite functions.

Also shown in FIG. 4 is a biometric sensor 414 attached to or worn by a user 416. In an alternate embodiment, the biometric sensor 414 is contained in the user system 402.

Technical effects and benefits include the ability to assign tasks based on biometric feedback about a user.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A method comprising:

receiving, by a processor, a request to assign a plurality of tasks of a project to a group of users located in a plurality of geographic locations;

accessing, by the processor, correlated data that correlates characteristics of tasks previously performed by each user in the group of users with their observed productivity and stress levels while performing the previous tasks, each observed stress level either a negative stress level or a positive stress level;

applying, by the processor, an optimization model to assign the plurality of tasks of the project to users in the group of users in a manner that maximizes a predicted productivity across the project while at the same time minimizes a predicted negative stress level across the project, wherein input to the optimization model includes the correlated data and characteristics of the plurality of tasks;

assigning the plurality of tasks of the project to users in the group of users based at least in part on output from the optimization model;

receiving, by the processor, an observed productivity of a user in the group of users while the user is performing one of the plurality of tasks;

collecting, by a biometric sensor, biometric data for the user in the group of users while the user is performing the one of the plurality of tasks, wherein the receiving the observed productivity of the user and the collecting biometric data for the user overlap in time;

calculating an observed stress level of the user while performing the one of the plurality of tasks based at least in part on the biometric data; and updating, by the processor, the correlated data for the user based on the observed productivity of the user in performing the one of the plurality of tasks, the observed stress level of the user while performing the one of the plurality of tasks, and at least one characteristic of the one of the plurality of tasks.

2. The method of claim 1, wherein the observed productivity is based on one or more of a comparison of an expected completion date and an actual completion date, and a comparison of an expected number of time units to complete the selected task and an actual number of time units to complete the selected task, and the updating the correlated data comprises:

based on the observed productivity, characterizing the observed stress level as a negative stress level or a positive stress level;

associating the observed stress level and observed productivity with the at least one characteristic of the selected task; and storing results of the associating.

3. The method of claim 2, wherein the associating takes into account a previous stress level and productivity associated with the selected task.

4. The method of claim 1, wherein the biometric sensor includes a Q-sensor that is attached to the user.

5. The method of claim 1, wherein the biometric sensor includes a heart-rate monitor that is attached to the user.

6. The method of claim 1, wherein the biometric sensor includes a pupil dilation detector.

7. The method of claim 1, wherein the biometric sensor includes two or more of a Q-sensor, a heart-rate monitor, and a pupil dilation detector.

8. The method of claim 1, wherein the updating the correlated data is further based on external factors about the user.

9. The method of claim 1, further comprising determining whether the user in the group of users has elected to allow collection of the biometric data for the user in the group of users, and wherein the collecting, calculating, and updating are performed based at least in part on determining that the user has elected to allow collection of the biometric data.

* * * * *